United States Patent [19]

Kakimoto

[11] Patent Number: 5,074,750
[45] Date of Patent: Dec. 24, 1991

[54] AIR MOTOR ASSEMBLY

[75] Inventor: Yasuo Kakimoto, Aichi, Japan

[73] Assignee: Ushio Co., Ltd., Aichi, Japan

[21] Appl. No.: 461,929

[22] Filed: Jan. 8, 1990

[51] Int. Cl.[5] .......................... F01D 1/00; A61C 1/00
[52] U.S. Cl. ................................ 415/200; 415/214.1;
415/904; 433/114
[58] Field of Search ...................... 415/202, 214.1, 904,
415/503, 182.1, 200; 417/359; 418/270;
433/114

[56] References Cited

U.S. PATENT DOCUMENTS

| | | | |
|---|---|---|---|
| 1,483,008 | 2/1924 | Ozanne | 433/114 |
| 2,570,009 | 10/1951 | Schmid | 418/270 |
| 3,083,946 | 4/1963 | Kern, Jr. | 415/202 |
| 3,309,965 | 3/1967 | Weickgenannt | 418/270 |
| 3,827,834 | 8/1974 | Kakimoto | 418/270 |
| 4,863,381 | 9/1989 | Kakimoto | 433/129 |
| 4,955,836 | 9/1990 | Suzuki et al. | 440/77 |

Primary Examiner—Edward K. Look
Assistant Examiner—Hoang Nguyen
Attorney, Agent, or Firm—Sandler, Greenblum & Bernstein

[57] ABSTRACT

An air motor assembly driven by compressed air for using pencil type handy grinder, comprising an outer jacket casing made of a synthetic resin to cover a metal-made cylindrical housing to house an air turbine cylinder having air jetting nozzles into the turbine rotor thereof and air discharging apertures at opposite side of the air jetting nozzles, the compressed air feeding passages provided along the axis to the air turbine cylinder and the discharged air exhausting passages provided in parallel with the air feeding passages, the feeding air control mechanism including an air valve tube with air communicating orifices and a flange shaped valve, an air controlling knob made of a synthetic resin having double cylindrical structure consisting of an inner cylindrical body and an outer cylindrical body which is to be inserted into the enlarged portion of the outer jacket casing to form the discharged air exhausting passage between the inner and outer cylindrical bodies, and a noise silencing baffler made of a fibrous material having a thick cylinder shape provided in the discharged air exhausting passage, whereby it can provide a thermally insulated and noiseless type air motor assembly.

5 Claims, 1 Drawing Sheet

U.S. Patent
Dec. 24, 1991
5,074,750
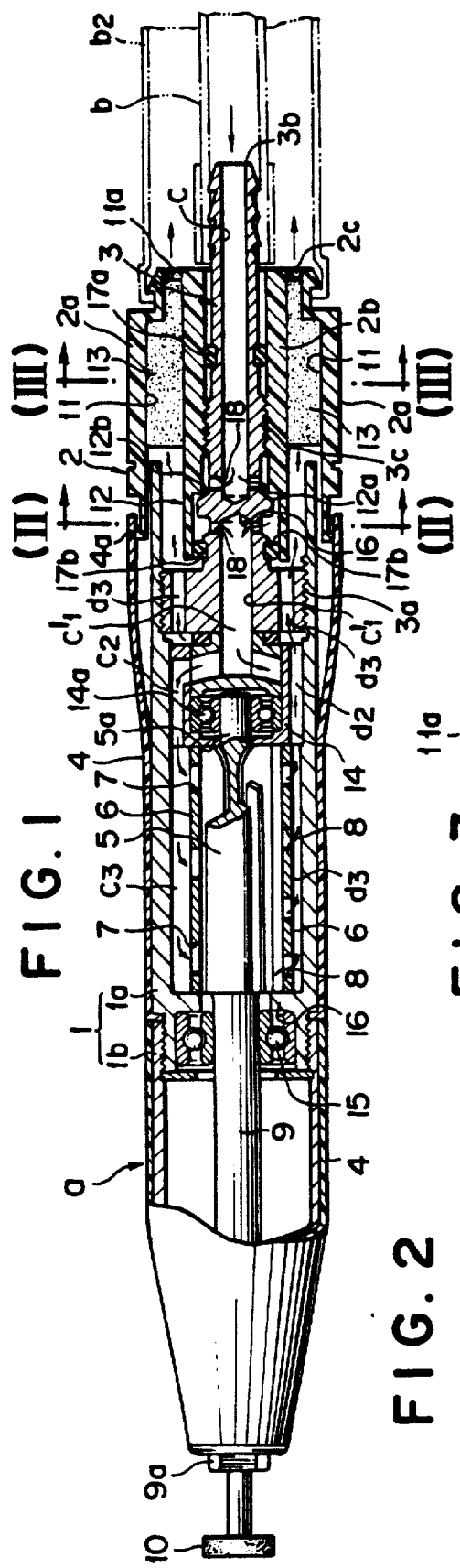
FIG. 1
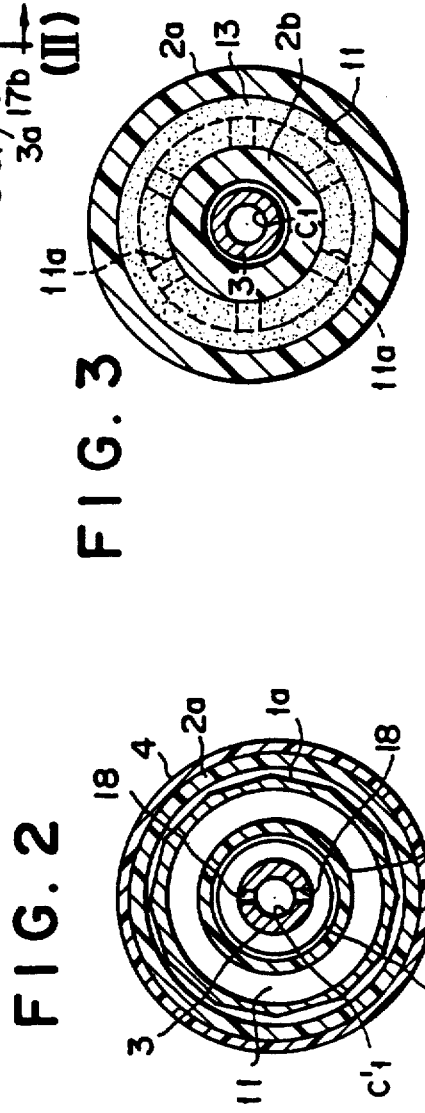
FIG. 2
FIG. 3
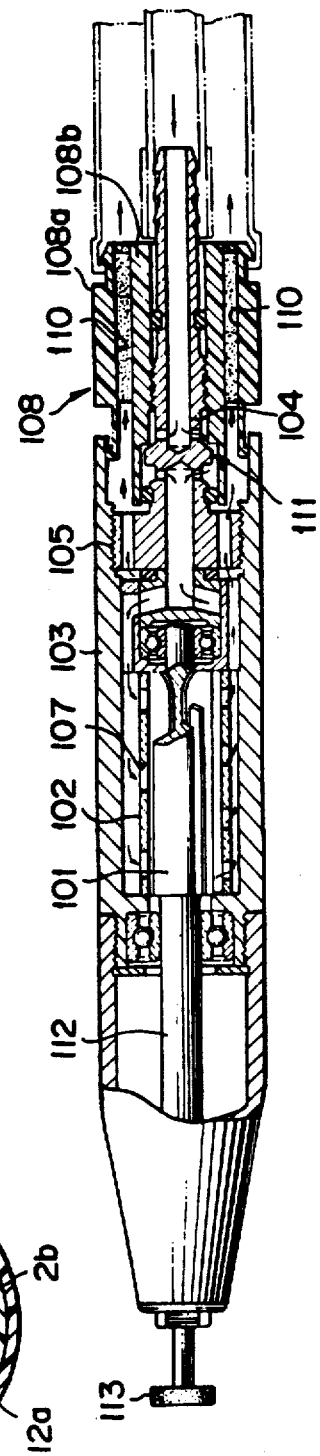
FIG. 4

AIR MOTOR ASSEMBLY

BACKGROUND OF THE INVENTION

1. Field of the Invention

This invention relates to an air motor, more particularly to a pencil typed air turbine motor driven by compressed air for us as a power source of dental surgery air grinder and the like, and further particularly to an air motor capable of thermally insulating the circumferential overheating of an air-motor housing as well as reducing an exhaust air jet noise.

2. Description of the Prior Art

Conventionally in the prior art, as shown in FIG. 4, in an air motor used for a power source of an air grinder and the like, the motor housing (103) is formed by a metallic member which houses a turbine rotor(101) and a cylinder(102) within the housing, the threaded end portion(105) of a small sized valve tube(104) is screwed in the interior at the rear port of motor housing(103) to connect the valve tube(104) with the motor housing(103) integrally so as to communicate air fluidly between compressed air outlet orifices(106) provided in the valve tube(104) and air inlet apertures(107) provided in the cylinder(102).

An air controlling knob(108) is further screwed on the motor housing(103) so as to cover the outer periphery of valve tube(104). The air controlling knob(108) has a double cylinder structure consisting of an inner cylinder(108b) and an outer cylinder(108a), and the end opening portion of the inner cylinder(108b) is inserted rotatably into the inner circumference at the rear opening portion of motor housing(103) by screwing the outer threaded portion of valve tube(104) in the inner threaded portion of inner cylinder(108b).

The air controlling knob(108) has a annular shaped space in its cross-section between the inner cylinder(108b) and the outer cylinder(108a), the annular shaped space consists of an air exhaust passage(110) which discharges the exhaust air backward from air exhaust ports (109) of the cylinder(102), wherein the compressed air supplying rate is controlled by opening or closing an air control valve(111) which is located between the inner cylinder(108b) of the air controlling knob(108) and the valve tube(106) according to the rotative adjustment of air controlling knob(108).

The above conventional motor, however, has such disadvantage that the air motor normally generates a considerable quantity of various heat, which consist of heat such as the air which heats as compression heats in its compressor and air turbine portion according to the hydrodynamic theory, the friction heat of air turbine rotor(101) and its shaft, the heat of power output shaft with chuck(112) and its working instruments such as a drill or grinder and the like during their respective high speed rotation, although their generated heat are cooled down reciprocatingly by various cooling factors such as the high speed air passing through and within the exhausting passage(109) of cylinder(102) after the rotating work of air turbine rotor(101), heat radiation upon all the surface of pipe line lengthened from an air compressor and the like.

According to a field report from users, however, it is recognized that the extent of the cooling is often dependent on the room temperature of the working location. For example, in case of the airmotor being used in such an environment having a comparatively higher room temperature, it is observed that the surface temperature of the airmotor made of the metallic member gradually rises and becomes too hot for the user due to the material properties of airmotor housing(103) made of the metallic member having a high ratio of specific heat and the lower cooling capacity of air blow inside from the high room temperature.

In contrast, when the room temperature is lower, it is reported that the motor housing(103) becomes too cold for the user. From these circumstances in the conventional motor, it is disadvantageous in that the user is compelled to handle the air motor equipment with the temperature fluctuation of air-motor housing(103).

Another disadvantage of the conventional motor is the noise problem due to the high speed exhaust air jet from the air exhaust passages(109)(110) of the housing(103). Reviewing the structure of the conventional type air controlling knob(108), that originally the annular space portion of exhaust air passage(110), which is provided between the inner cylinder(108b) and the outer cylinder(108a) of air controlling knob(108), has a similar structure of a silencer such as the muffler of internal combustion engine as a silencer of exhaust gas jet noise. However, in the actual problem of the conventional motor, the silencer effect is very low because of the lack of muffler space capacity. The reason of the lack is that the diameter of a pencil type air motor should be smaller as much as possible so that the diameter of air controlling knob(108) is also required to meet with the diameter of the motor housing(103) so as to be able to slidably insert the knob(108) into the rear end port of housing(103), thus the annular space portion of exhaust air passage(110) must be restricted according to the restricted diameter of air controlling knob(108). For the above reason, any noise which is the so-called a supersonic wave type noise to be produced by the air flow having too high speed at each noise generating portions such as the air outlet orifices(106), the air inlet apertures (107), an air exhaust passage(109), the air exhaust passage(110), and the like, cannot be avoided. As another noise producing source is caused by the slidably connecting portion formed between the end port of inner cylinder(108b) and the internal circumference of outer cylinder(108a) where the highly compressed air often leaks out partially from the overlapped portion between the inner cylinder(108b) and the outer cylinder(108a). As a further noise source, the high speed rotating turbine rotor(101) produces a supersonic wave type noise together with covibration with the metallic housing body(103) to produce a resonance noise.

SUMMARY OF THE INVENTION

According to the present invention, a novel thermal-insulation technique is provided which avoids an overheating or over cooling of an air motor housing. In addition a noise silencer technique is provided which improves a silencer effect in an air exhaust passage by enlarging the passage space and also which reduces the air exhausting noise by preventing air leakage from an overlapped connecting portion of an air controlling knob.

OBJECTS AND ADVANTAGES OF THE INVENTION

Accordingly, it is an object of the present invention to provide an air turbine motor comprising:

an outer jacket casing made of a synthetic resin provided to cover a metal-made housing which houses an turbine cylinder with an air turbine rotor therein;

an air valve tube connected with the metallic housing integrally by screwing the air valve tube into the rear end opening of the metallic housing, which communicates air fluidly between air communicating orifices provided in the air valve tube and an air inlet aperture provided in the turbine cylinder;

an air controlling knob having a double cylindrical structure, which consists of an outer cylindrical body and an inner cylindrical body, which is connected with the air valve tube by screwing the air controlling knob on the threaded outer circumference of the air valve tube, and which consists of a valve for adjusting the air supply rate to open or close the air supply orifices according to the inner cylindrical body and the air valve tube;

a discharged air exhausting passage provided between the inner cylindrical body and the outer cylindrical body to discharge backward the exhaust air from the air exhaust aperture of the turbine cylinder; and an enlarged rear portion in diameter of the outer casing provided to connect with the outer cylindrical body of the air controlling knob by inserting the end opening portion of the outer cylindrical body into the rear end opening of the outer casing closedly so as to be able to screw in or screw out.

It is a further object of the present invention to provide an air turbine motor comprising:

a thermally insulating outer jacket casing provided to cover on the outer circumference of the metallic housing, which is made of a synthetic resin having considerable insulation properties, wherein the outer casing can reduce the heat transmission between the temperature increased metallic housing and the user's hand as well as reducing the covibration noise generated from the air turbine assembly;

an enlarged air exhausting passage provided within the air controlling knob having the double cylindrical structure, which is formed as an annular space in cross section between the inner cylinder and outer cylinder of the air controlling knob, wherein the enlarged air exhausting passage can facilitate the air flow in the air exhausting passage to improve air exhausting efficiency as well as a silencer effect according to the decompression of exhaust air caused by enlargement of the passage;

a double cylindrical structure of the air motor housing provided at the rear opening of the housing, consisting of the outer casing cylinder with the enlarged diameter more than the air turbine cylinder portion and the metallic housing cylinder, which provides an annular space in cross section formed between the outer casing and the metallic housing as well as the annular space of the air controlling knob; and the end opening portion of the outer cylinder provided at the front side of the air controlling knob, which is a plastic thin cylinder inserted into the annular space formed between the outer casing and the metallic housing so as to contact tightly the outer circumference of the outer cylinder with the inner circumference of the outer casing cylinder by screwing the inner cylinder on the air valve tube.

BRIEF DESCRIPTION OF THE DRAWINGS

FIG. 1 is a vertical front view for showing an air turbine motor practiced preferably in the present invention, FIG. 2 is a section view taken along line II—II in FIG. 1, FIG. 3 a section view shown by line III—III in FIG. 1 and FIG. 4 is a vertical front view for showing a conventional air turbine motor.

DESCRIPTION OF THE PREFERRED EMBODIMENT

Referring now in detail to an air motor assembly of the present invention in accordance with the drawings.

In FIG. 1 to FIG. 4, an air motor assembly is shown which is usable as the driving source of an air grinder for industry use or dental use, in outline which consists of a housing(1), an air turbine cylinder(6), a turbine rotor(5), a rotor shaft(9) and a working tool(10). In operation, compressed air is introduced from an air supply hose(b) connected with the rear end of an air motor body(a) into the air turbine cylinder(6) housed within the housing(1) through air supply passages, wherein the turbine motor(5) and the rotor shaft(9) with the working tool(10) are forcibly rotated in high speed rotation by jetting the compressed air toward the turbine rotor(5).

The exhaust air which was used for driving the turbine rotor(5) is discharged backward through an exhaust air passage(11) located at the rear end of the air motor body(a) to the outside.

In FIG. 1, the housing(1) is formed as mostly a pencil shape, and made of a metallic material such as aluminum and the like, which consists of a cylindrical body portion(1a) having a regular polygon shape of outer circumference in cross section view (FIG. 2) and a tapered stem portion(1b), wherein both portions are detachably screwed together, and the turbine rotor(5) with the rotor shaft(9) is supported along with the axis therein.

In FIG. 1, the turbine system such as the turbine rotor(5), the rotor shaft(9) and a rear support shaft(5a) are formed integrally, and the rotor shaft(9) is held with ball bearing (15) fitted into a bearing bed provided at the outer threaded engagement portion of the front end of cylindrical body portion(1a) in which is engaged with the inner threaded stem portion (1b). On the other hand the rear ball bearing(14a) is fitted into a bearing bed provided in a support block(14) which is inserted from rear side, whereby the turbine rotor(5) is supported between the rotor shaft(9) which is held by the bearing(15) and the rear support shaft(5a) which is held by the rear bearing(14a) so as to smoothly rotate at high speed. In addition, the rotor shaft(9) provides a tool chuck(9a) for chucking the working tool(10).

In regard to the turbine cylinder(6), it provides a plurality of air jetting nozzles(7) aligned in parallel with the axis on the circumferential surface of turbine cylinder(6), besides a plurality of a discharged air exhausting apertures(8) are opposed to the air jetting nozzles(7) in aligned manner on the opposite surface of turbine cylinder(6).

The turbine rotor(5) is arranged to be positioned eccentrically in the turbine cylinder(6) in cross section view so as to be spaced more widely in the air compression area between the upper level of turbine rotor(5) and the air jetting nozzles(7). In contrast, the bottom level of turbine rotor(5) closes up the discharged air exhausting apertures(8), and is also arranged to be positioned between the partition wall of a support block(14) and the opposite partition wall(16) according to the technique of pneumatic mechanics.

In FIG. 1, it provides an air valve tube(3), which consists of a small size tube portion(3b) for introducing compressed air from the air supply hose(b) to the turbine cylinder(6) and an outer thread flange portion(3a) which is to be engaged with an inner threaded portion of cylindrical body portion(1a) in the interior from the rear end opening of cylindrical body portion(1a). As shown in FIG. 1, the air valve tube(3) is blocked off at the middle position of the tube by a partition wall(16') formed between both sides air feeding passages(C1)(C'1) where there is a flange shaped valve(12a) formed projectedly around the circumference of partition wall(16') and also a plurality of air communicating orifices(18)(18') formed in both sides at the flange shaped valve(12a). Although it will be described in detail hereafter, there is an air controlling knob(2) which is separate from the housing(1) and which consists of a double cylindrical structure such as an inner cylinder body(2b) and an outer cylinder body(2a), wherein step portion(12b) is provided with the inner cylinder body(2b).

Again referring back to the structure and function of air valve tube(3), the air flow rate is controlled by moving forward or backward the step portion (12b) of inner cylinder body(2b). When the step portion(12b) contacts the flange shaped valve(12a), the air flow is stopped between both orifices(C1)(C'1) and the rotation of turbine rotor is also stopped. This is the basic mechanism of the air valve tube in combination with the step portion, that is, the air controlling knob(2).

As described previously, the air controlling knob(2) consists of the inner cylinder body(2b) provided to cover the air valve tube(3) by engaging the inner threaded portion of inner cylinder body(2b) with the outer threaded portion of air valve tube(3) and the outer cylinder body(2a) provided to further cover the outer circumference of inner cylinder body(2b) with a concentric space between the inner and outer cylinder bodies(2b)(2a) which is used for an exhaust air passage (11).

Both inner and outer cylinder bodies(2a)(2b) are formed to incorporate each other at the rear end portion of both cylinders(2a)(2b) by a plurality of supporting stays(2c) extending radially at right angles relative to the axis line of the cylinders. In the interior of the inner cylinder body(2b), an internal thread is provided therein which engages the outer thread portion (3c) provided at the middle position of the air valve tube(3) through a packing ring(17a) such as O-ring and the like, provided around the circumference of the tube(3).

By screwing the air controlling knob(2) into the rear end opening of cylindrical body portion(1a), the front end opening portion of the inner cylinder body(2b) is slidably inserted into the rear end opening of the cylindrical body portion(1a) as well as the front end opening portion of the outer cylinder body(2a) being also slidably inserted into the outer circumference of the rear end opening of the body portion(1a).

The front end opening portion of the outer cylindrical body(2a) of the air controlling knob(2) is formed as a thin core cylinder made of a synthetic resin having a resilience to facilitate the insertion of the front end opening portion into the annular shaped aperture(4a), further this front end opening portion has a small flange shaped brim formed to project outward around at the edge of the front end opening to effect an air-tight structure by contacting the brim with the inner circumference(4a) of the enlarged opening portion of the outer jacket casing(4) so as to slidably rotate the knob(2) without any air leakage from the inside of the discharged air exhausting passage(11) according to the air-tight structure.

As previously referred to, the steps portion(12b) is formed in the inner peripheral surface of the inner cylinder body(2b), which comprises the air controlling knob(2) by opposing the step portion(12b) against the flange shaped valve (12a). According to the rotation of the air controlling knob (2) toward the axis direction, a clearance formed between the step portion(12b) and the flange shaped valve(12a) is changed wherein the air flow rate communicating within the inner cylinder body(2b) over the flange shaped valve(12a) held between the both orifices(18)(18') can be preferably controlled. Again referring to the air flow channel between the connection port(3b) of air valve tube(3) and the air jetting nozzles(7) on the turbine cylinder(6), the compressed air is supplied into the air jetting nozzles(7) finally through the connection port(3b) and rear air passage(C1) of the air valve tube(3a), the air outlet orifices(18) and air inlet orifice(18') over the flange shaped valve(12), a front air passage(C'1), a branched air passages(C2) formed in the supporting block(14) and the outer peripheral air passage(C3) formed along the turbine cylinder(6).

The compressed air jetted from the air jetting nozzles(7) into the turbine cylinder(6) after passing through the air supply channel gives the motive power of rotation to the turbine rotor(5), thereafter the used air is discharged to the discharged air exhausting passage(11) finally through the discharged air exhausting apertures(8), the first exhaust passage(d1) formed under the bottom of the turbine cylinder(6), the second exhaust passage(d2) formed under the bottom of the supporting block(14) with a clearance provided vertically between the rear end wall of the supporting block(14) and the front end of air valve tube(3) and the third exhaust passage(d3) formed within the core portion between the front air passage(C'1) and the outer thread flange portion(3a) of the air valve tube(3).

Referring now in detail to the discharged air exhausting passage(11), this passage(11) not only to provide a smooth exhaust of the air but also to improves a silencer effect from the supersonic-wave type air jet noise. From these multi-purposes, the discharged air exhausting passage(11) consists of the space of dumping the noise as a muffler, which is formed between the outer circumferential surface of the inner cylinder body(2b) to be engaged on the outer circumference of the air valve tube(3) and the inner circumference surface of the outer cylinder body(2a) to engage the front end opening onto the outer circumferential surface of the cylindrical body portion(1a).

As a positive means for silencing the noise, cylinder shaped silencing material(13) is housed tightly within the space of the discharged air exhausting passage(11), which is made of a fibrous material having air permeable porosity, wherein the exhaust air is introduced to pass through the silencing material(13) and discharged from the tail end exhaust ports(11a) located at the rear end portion of the air controlling knob(2) into an exhaust hose(b2) connected with the tail end portion of the air controlling knob(2).

Referring now in detail to the space capacity of the discharged air exhausting passage(11), the present invention can provide an enlarged exhaust air passage due to the enlargement of diameter of the outer cylinder body(2a) in comparison with the conventional type without any enlargement of the housing diameter at the rear end portion as shown in FIG. 4.

According to the enlargement of the diameter, the space capacity of the discharged air exhausting passage(11) is enlarged so that the silencing effect is improved according to the sudden inflation of the air released in the enlarged space instead of those tight passages such as the passages(d1) and (d2) with the decompression of the air caused in the enlarged passage(11). According to such multiple effects between the use of the noise baffler as a silencer and the adiabatic expansion of the compressed air in the enlarged passage(11), the present invention solves the noise problem.

Referring now to the heat insulation structure of the present invention, as mentioned previously, the outer jacket casing(4) is made of a synthetic resin having a good insulation properties, and which is divided into two parts such as the tapered stem portion(1b) and the cylindrical body portion(1a) as well as in case of the metallic housing(1). These outer jacket casings(4) are jacketed over the tapered stem portion(1b) of the metallic housing and the cylindrical body portion(1a) respectively and fixedly so that the outer jacket casing(4) can prevent the temperature fluctuation of the metallic housing(1) according to the change of environmental temperatures. In the formation of the outer jacket casing(4), it is formed that the rear end opening portion of the outer jacket casing(4) is enlarged outwardly so as to provide a annular aperture between the enlarged opening(4a) of the outer jacket casing(4) and the outer circumference of the metallic housing(1), wherein the front end opening portion of the outer cylinder body(2a) is inserted tightly into the annular aperture formed between the enlarged opening(4a) and the outer cylinder body(2a). By inserting the front end opening portion into the annular aperture tightly, it can prevent not only the temperature fluctuation of the surface as referred to previously but also the air leakage from the overlapped portion between the enlarged opening portion(4a) and the outer cylinder body(2a) according to the assistance given by the decompression of the exhaust air in the enlarged passage (11), which also prevents the local noise generation by the air leakage at the overlapped place as in the conventional motor. It has been measured experimentally that this jacket casing(4) shows approximately 25% less of noise dumping effect in comparison between the present invention and the conventional type products in the case of the inventor's own products.

Modifications may be made in practicing the invention modified by the use of different means. Accordingly it is not intended to have the invention limited to or circumscribed by the specific details of procedure, materials, proportions herein as above set forth by way of example in view of the fact that the invention is susceptible to modifications according to individual preference or conditions without departing from the spirit of this disclosure and the scope of the appended claims.

What is claimed is:

1. An air motor assembly driven by compressed air, including a metal cylindrical housing consisting of tapered stem and body portions, an air turbine cylinder with a power output shaft, air supply and exhaust passages, a feed air controlling knob having said air supply and exhaust passages therein and being connected with said cylindrical housing, said air motor assembly comprising: an outer jacket casing having an enlarged diameter at a rear end opening portion thereof, said casing being made of a synthetic resin, said casing comprising said metal cylindrical housing provided to house a turbine rotor and a turbine cylinder; an air valve tube provided to integrally connect with the interior of the rear end opening of said housing wherein a compressed air feeding passage formed in said air valve tube communicates with an air feeding port of said turbine cylinder; said feed air controlling knob having a double cylindrical structure consisting of an inner cylindrical body and an outer cylindrical body, which is provided to engage by screw means with the outer circumference of said air valve tube so as to form an air adjusting valve for controlling said compressed air feeding passages to close or open the valve according to the combination with said inner cylindrical body and said air valve tube, as well as to form a discharged air exhausting passage between said inner cylindrical body and said outer cylindrical body to discharge the exhaust air backward from an air exhausting port of said turbine cylinder, and the front end opening of said outer cylindrical body being inserted into an annular shaped aperture formed between the outer circumference of said metal cylindrical housing and the inner circumference of the rear end opening portion of said outer jacket casing having said enlarged diameter portion thereof so as to slidably rotate said knob without any air leakage from the inside of said passage because of the air-tight structure of the front end edge portion of said outer cylindrical body.

2. The air motor assembly according to claim 1, wherein said metal cylindrical housing has a polygon shaped circumference providing a plurality of circular arc shaped spaces between said outer jacket casing and said housing so as to thermally insulate heat transmission outward in combination with said synthetic resin outer jacket casing.

3. The air motor assembly according to claim 1, wherein said air controlling knob is made of a synthetic resin.

4. The air motor assembly according to claim 1, wherein a noise silencing baffler is inserted into said discharged air exhausting passage and is shaped as a cylindrical shaped having a core thickness to correspond with the width of said discharged air exhausting passage.

5. The air motor assembly according to claim 3, wherein said front end opening portion of said outer cylindrical body of said air controlling knob is formed as a thin core cylinder having a resilience to facilitate the insertion of said front end opening portion into said annular shaped aperture, said front end opening portion has a small flange shaped brim formed to project outward around the edge of said front end opening to effect the air-tight structure by contacting said brim with said inner circumference of said enlarged opening portion of said outer jacket casing.

* * * * *